United States Patent [19]

Baumann et al.

[11] B 4,001,017

[45] Jan. 4, 1977

[54] PROCESS FOR THE PHOTOPOLYMERIZATION OF ETHYLENICALLY UNSATURATED COMPOUNDS

[75] Inventors: Niklaus Baumann, Fribourg; Hans-Peter Schlunke, Marly, both of Switzerland

[73] Assignee: Ciba-Geigy AG, Basel, Switzerland

[22] Filed: Nov. 29, 1973

[21] Appl. No.: 420,176

[44] Published under the second Trial Voluntary Protest Program on March 16, 1976 as document No. B 420,176.

[30] Foreign Application Priority Data

Dec. 5, 1972   Switzerland .................... 17658/72

[52] U.S. Cl. .............................. 96/35.1; 96/115 P; 204/159.23; 204/159.24
[51] Int. Cl.$^2$ ......................................... G03C 1/70
[58] Field of Search .................. 96/115 P, 35.1; 204/159.23, 159.24

[56] References Cited

UNITED STATES PATENTS

| 3,531,282 | 9/1970 | Miller et al. | 96/115 P |
| 3,765,898 | 10/1973 | Bauer et al. | 96/115 P |

*Primary Examiner*—Ronald H. Smith
*Attorney, Agent, or Firm*—Joseph G. Kolodny; Edward McC. Roberts; Prabodh I. Almaula

[57] ABSTRACT

In photopolymerization, the polymerization process is activated or initiated by radiation, for example in the region of ultraviolet or visible waves. According to the present invention ethylenically unsaturated compounds can now be polymerized advantageously with the aid of a new catalyst system which consists of a diazine compound, preferably a quinoxaline and an electron donor, which together act as a photoredox pair.

14 Claims, No Drawings

PROCESS FOR THE PHOTOPOLYMERIZATION OF ETHYLENICALLY UNSATURATED COMPOUNDS

In photopolymerisation, the polymerisation process is activated or initiated by radiation, for example in the region of ultraviolet or visible waves. According to the present invention ethylenically unsaturated compounds can now be polymerised advantageously with the aid of a new catalyst system which consists of a diazine compound, preferably a quinoxaline and an electron donor, which together act as a photoredox pair.

In the present process for the photopolymerisation of ethylenically unsaturated compounds with the aid of at least one photoredox pair, the redox pair employed is, on the one hand, a diazine compound containing the ring system of the formula (1) 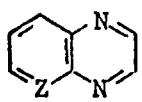

wherein Z denotes a nitrogen atom or a carbon atom bonded to a hydrogen atom or a substituent, which diazine compound can also be quaternised and, on the other hand, an electron donor. The radiation used for the photopolymerisation lies in the range of 200 to 450 nm.

A large number of non-quaternary diazine compounds suitable for the present process are known. These are, for example, quinoxalines, pyrazines or phenazines, including benzophenazines. They can be manufactured according to known methods. Compare, on this topic, A. C. E. Simpson, Condensed Pyridazines and Pyrazine Rings in A. Weissberger, The Chemistry of Heterocyclic Compounds J. Wiley & Sons, New York (1953); G. A. Swan & D. G. Felton, Phenazines in A. Weissberger, ibid. (1957); Y. T. Pratt in R. C. Elderfield, Heterocyclic Compounds, J. Wiley & Sons, New York 1957, Vol. 6, page 377 et seq.; D. E. Pearson, ibid., page 624 et seq.; J. P. Horwitz, ibid., 1961, Vol. 7, page 720 et seq.)

Preferably, diazine compounds of the formulae (2) to (13) are used in the present process:

(2) 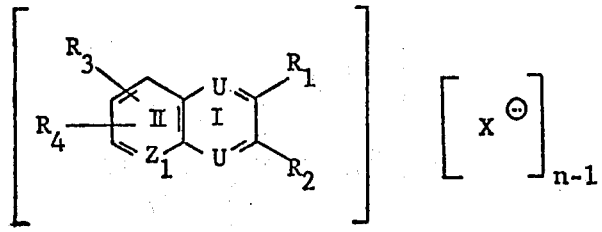

(3) 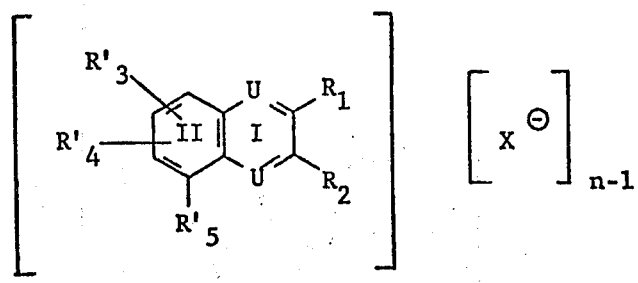

(4) 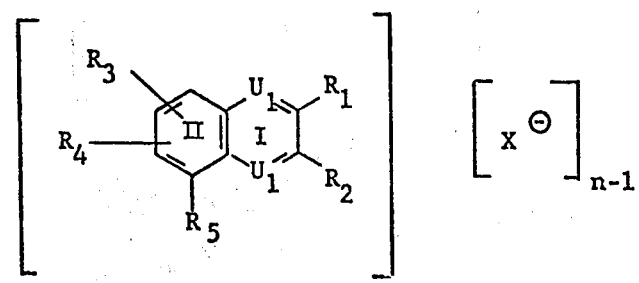

(5) 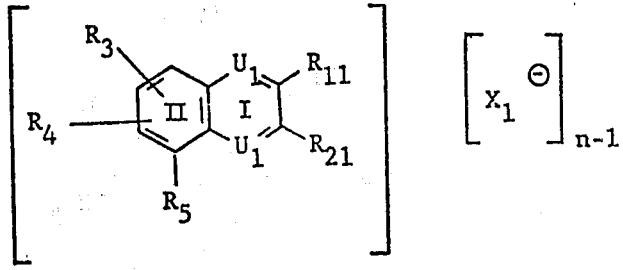

(6) 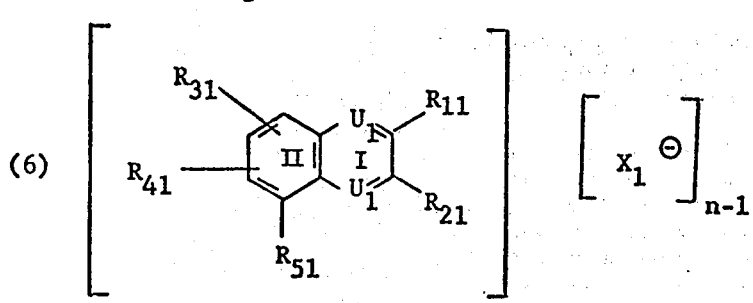
(7) 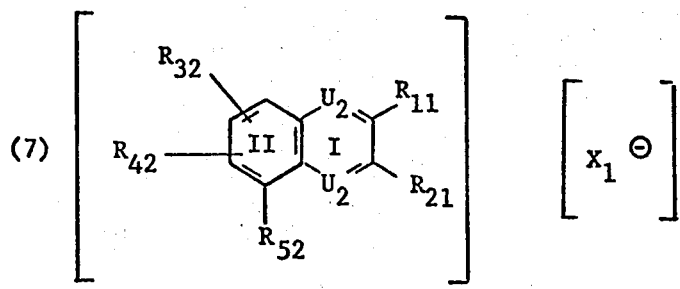
(8) 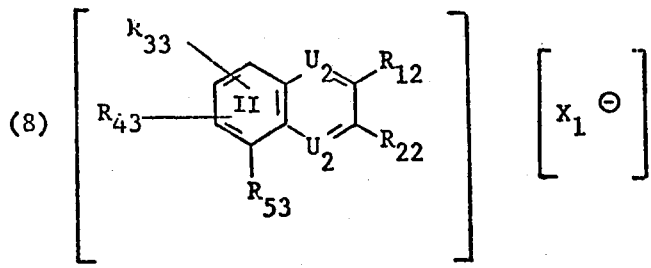
(9) 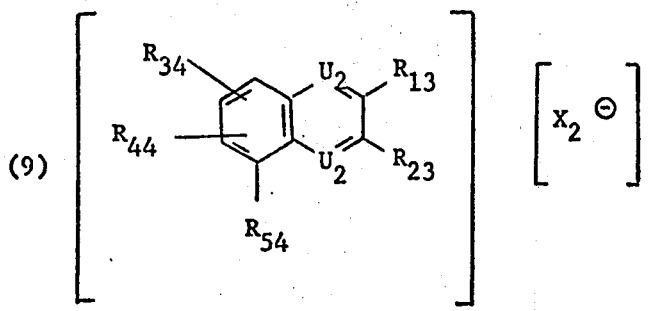
(10) 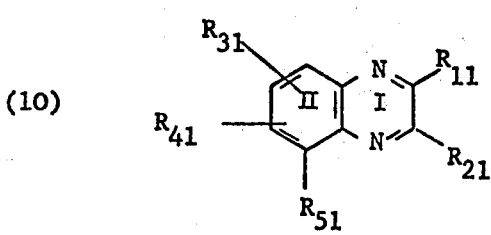
(11) 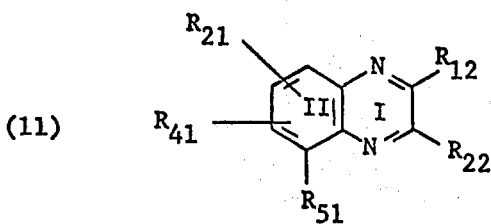

(12) 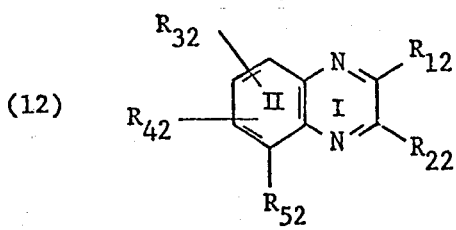

(13) 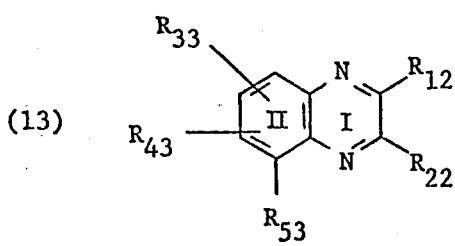

If the compounds of the above formulae (2) to (8) are quaternary (n=2, U = ≫ N—Y, see below), there are in each case two possible isomers of the cation, for example:

(14.1) 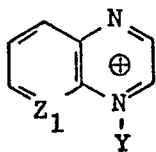

and (14.2) 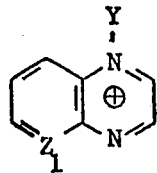

($Z_1 \ne$ CH).

In the formulae, the individual symbols have the same meaning throughout, namely the following:

n — one of the numbers 1 and 2, $Z_1$ — a nitrogen atom or a

group (for $R_5$, see below)

U, U — one U a nitrogen atom and the other U, if $n = 1$, also a nitrogen atom, and if $n = 2$, a group of the composition

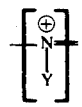

Y — an alkyl radical which is optionally substituted further, $U_1$, $U_1$ — one $U_1$ a nitrogen atom and the other $U_1$, if $n = 1$, also a nitrogen atom, and if $n = 2$, a

group, $U_2$, $U_2$ — one $U_2$ a nitrogen atom and the other $U_2$ a

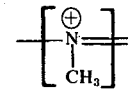

group, $R_1$, $R_2$ — independently of one another, a hydrogen atom, an alkyl, alkoxy, aroyl, aryloxy or aralkoxy radical which is optionally substituted further (possible substituents on alkyl groups are, for example, halogen atoms, acylamino, acyloxy, hydroxyl, alkoxy, alkylsulphuryl, alkylthionyl, nitrile, carboxylic acid alkyl ester and carboxylic acid amide groups, and possible substituents on aryl radicals, preferably benzene radicals, are methyl groups, halogen atoms, such as chlorine, methoxy groups, acylamino, acyloxy, hydroxyl, trialkylsilyl, carboxylic acid alkyl ester, carboxylic acid amide, alkylsulphuryl, alkylthionyl, arylsulphuryl, arylsulphonyl, nitrile and sulphonic acid groups); or $R_1$ and $R_2$ together with two carbon atoms of the ring I, a heterocyclic or isocyclic ring (for example a ring of the formulae

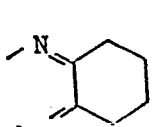

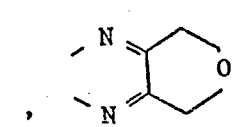

$R_{11}$, $R_{21}$ — a benzene radical which may or may not be substituted further (see above, $R_1$, $R_2$), a benzoyl group, a methyl group which is optionally substituted further, or a hydrogen atom; or $R_{11}$ and $R_{21}$ together with two carbon atoms of the ring I, a five-membered to six-membered heterocyclic or isocyclic ring, $R_{12}$, $R_{22}$ — a phenyl group, a benzoyl radical, a phenylsulphonic acid group, a hydroxymethyl group or a hydrogen atom, $R_{13}$, $R_{23}$ — both a phenyl group or both a methyl group, $R_3$, $R_4$, $R_5$ — independently of one another, a hydrogen atom, an alkyl, alkoxy, aryloxy or aralkoxy radical which is optionally substituted further (with regard to substituents see above, $R_1$, $R_2$), a halogen atom, a nitro group, a nitrile group, a hydroxyl group, an amino group which is optionally substituted further (for example an acylamino group, monoalkylamino or dialkylamino group), an alkylammonium group, carboxylic acid group, carboxylic acid amide group, carboxylic acid alkyl ester group or sulphonic acid group, or two of $R_3$, $R_4$ and $R_5$ together with two adjoining carbon atoms of the ring II, an isocyclic or heterocyclic ring, $R'_3$, $R'_4$, $R'_5$ — one of these three symbols has any of the meanings indicated for $R_3$, $R_4$ and $R_5$, the second denotes a hydrogen atom, a halogen atom, an amino group, an alkyl group or an alkoxy group and the third denotes a hydrogen atom or an alkoxy group, or two of these symbols are members of a ring of the indicated composition and the third denotes a hydrogen atom or an alkoxy group.

An analogous choice of the substituents $R_{31}$, $R_{41}$, $R_{51}$ is also preferred in the case of the diazine compounds of the formulae (4) to (9) etcetera.

$R_{31}$, $R_{41}$, $R_{51}$ — a hydrogen atom, a lower alkyl group, a lower alkoxy group, a chlorine atom, a nitro group, a primary amino group, an acylamino group (such as acetyl, propionyl or benzoyl), a trimethylammonium group, a carboxylic acid amide group which is optionally substituted further by one or two lower alkyl groups, a carboxylic acid, carboxylic acid methyl ester or carboxylic acid ethyl ester or sulphonic acid group, or two of $R_{31}$, $R_{42}$ and $R_{51}$ together with two adjacent carbon atoms of the ring II, an isocyclic or heterocyclic ring (lower alkyl groups are those with at most 4 carbon atoms), $R_{32}$, $R_{42}$, $R_{52}$ — a hydrogen atom or a methyl, methoxy, ethoxy, nitro, amino, acetylamino, trimethylammonium or sulphonic acid group, or two of $R_{32}$, $R_{42}$ and $R_{52}$ together with two adjacent carbon atoms of the ring II, an isocyclic or heterocyclic ring, $R_{33}$, $R_{43}$, $R_{53}$ — a hydrogen atom, or a methyl, methoxy, ethoxy, nitro, amino, trimethylammonium or sulphonic acid group, or two of $R_{33}$, $R_{43}$ and $R_{53}$ together with two adjacent carbon atoms of the ring II, a dioxole, dioxane or pyridine ring, $R_{34}$, $R_{44}$, $R_{54}$ — a hydrogen atom, a methyl group or a methoxy group, X — an anion.

$X_1^-$ — one of the anions $Cl^-$, $I^-$, $ClO_4^-$, $CH_3SO_4^-$, $FSO_3^-$, $BF_4^-$, $PF_6^-$ and $AsF_6^-$, $X_2^-$ — one of the anions $I^-$, $ClO_4^-$ and $CH_3SO_4^-$.

Compounds which contain sulphonic acid groups or carboxylic acid groups can not only be in the form of their free acids, that is to say with HOOC— or $HO_3S$-groups but also in the form of salts. Depending on the conditions of isolation, for example the chosen pH value or the cation which the salt used for isolating the compound contains, the acid groups can be in the form of —$SO_3$-cation or —COO-cation groups, such as, for example, —$SO_3Na$, —$SO_3K$, COONa, —COOLi or —$COONH_4$. Preferably the compounds are thus, apart from the free acids, salts of the alkaline earth metal group or especially of the alkali metal group. The terms "carboxylic acid" and "sulphonic acid" are to be understood in this sense here.

Attention should also be drawn to the following publications wherein diazine compounds of the initially indicated composition and processes for their manufacture are described:

DT-OS 2,144,297
DT-OS 2,144,298
DT-OS 2,010,280

As examples of the anions ($X^-$) there may be mentioned: $Br^-$, $Cl^-$, $I^-$, $ClO_4^-$, $CH_3SO_4^-$, $BF_4^-$, $TiF_4^-$, $FSO_3^-$, $AlCl_4^-$, $FeCl_4^-$, $PF_6^-$, $SbCl_6^-$, $SbF_6^-$, $SiF_6^-$, p-toluenesulphonate$^-$, p-chlorobenzenesulphonate$^-$, oxalate$^-$, $SCN^-$, acetate$^-$, $HSO_4^-$, $AuCl_4^-$, $SnCl_4^{-2}$, $ZnCl_4^{-2}$, $AsF_6^-$ and $AsCl_6^-$.

In general, water-soluble diazine compounds are preferred, especially those with a solubility in water of at least 0.05% (g of diazine in 100 g of aqueous solution) at 20°C.

Examples of such water-soluble diazines are the phenylsulphonic acid quinoxalines of the formula

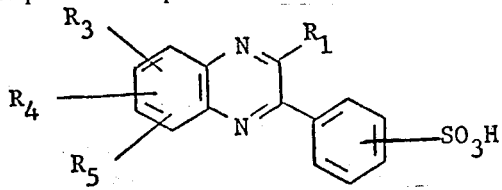

which can be manufactured by treating the corresponding compound which is free of sulphonic acid groups with chlorosulphonic acid at a low temperature and saponifying the sulphonic acid chloride thus obtainable. This gives a mixture of 2-phenyl-quinoxaline-3'- and -4'-sulphonic acids which can, if desired, be resolved into its components or can also be used as such for photopolymerisation according to the invention.

The quaternary quinoxaline compounds are also new, for example those of the formulae (15) to (18), which also form a subject of the present invention:

A. Quinoxalinium salts of the formula

(15) 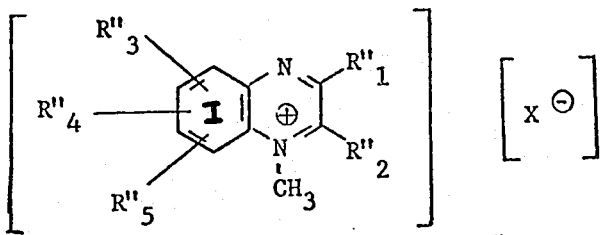

wherein $R''_1$ and $R''_2$ denote hydrogen atoms, or alkyl or aryl radicals which are optionally substituted by halogen atoms or alkyl, hydroxyl, alkoxy, nitro, amino, nitrile, carboxylic acid, carboalkoxy or carboxylic acid amide groups, $R''_3$, $R''_4$ and $R''_5$ independently of one another denote hydrogen atoms, halogen atoms or alkyl, alkoxy or nitro groups, with at least one of $R''_3$, $R''_4$ and $R''_5$ differing from hydrogen, and $R''_3$ and $R''_4$ or $R''_4$ can also together form the supplementary structure required to form a heterocyclic ring fused to the six-membered ring I and X denotes an anion.

B. Quinoxalinium salts of the formula

(16) 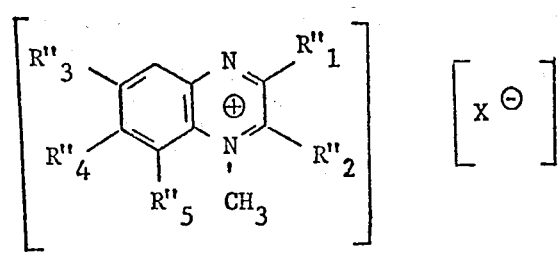

wherein R''₁, R''₂, R''₃, R''₄, R''₅ and X have the indicated meaning.

C. Quinoxalinium salts of the formula

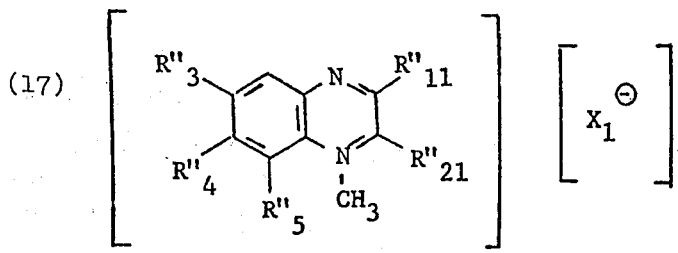

(17)

wherein R''₃, R''₄ and R''₅ have the indicated meaning, R''₁₁ and R''₂₁ denote hydrogen atoms, methyl groups, acetoxymethyl groups or phenyl radicals which are optionally substituted further and $X_1^-$ denotes one of the anions $Cl^-$, $I^-$, $ClO_4^-$, $CH_3SO_4^-$, $FSO_3^-$, $BF_4^-$, $PF_6^-$ and $AsF_6^-$.

D. Quinoxalinium salts of the formula

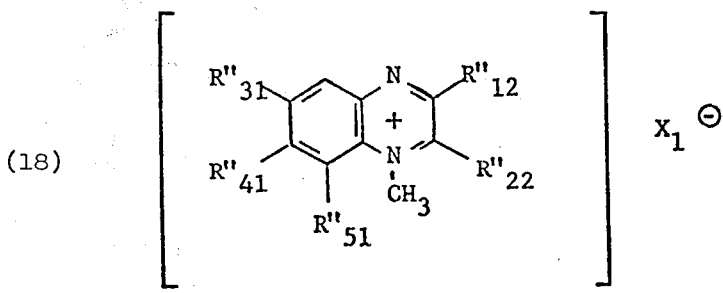

(18)

wherein $X_1^-$ has the indicated meaning, R''₁₂ and R''₂₂ denote methyl, acetoxymethyl or phenyl groups, R''₃₁, R''₄₁ and R''₅₁ independently of one another denote hydrogen atoms, chlorine atoms, methyl groups, methoxy groups, ethoxy groups, benzyloxy groups or nitro groups, with at least one of R''₃₁, R''₄₁ and R''₅₁ being different from hydrogen, and R''₃₁ and R''₄₁, or R''₄₁ and R''₅₁ can also together form the supplementary structure required to form a pyridine, dioxole or dioxane ring fused to the six-membered ring II.

These and other quaternary diazine compounds can be obtained by quaternising the corresponding bases. In particular, compounds of the formula (2), wherein Y denotes an alkyl group and n is 2, can be prepared by alkylation of the corresponding diazines (n = 1). This alkylation is in general carried out at elevated temperature and normal or elevated pressure. Examples of suitable alkylating agents are dialkyl sulphates such as dimethyl sulphate or diethyl sulphate and alkyl halides, especially iodides such as methyl iodide or ethyl iodide.

A particularly active alkylating agent is, for example, $CH_3SO_3F$, as described by M. G. Ahmed et al. (Chem. Comm. 1968, 1533).

If for any reasons it is desired to replace the anion $X^-$ in a quinoxalinium salt first formed, this can be effected without difficulty by double decomposition of the quinoxalinium salt with an appropriate salt in aqueous solution. If the desired salt does not precipitate directly, the precipitation can be effected by addition of an inactive water-miscible organic solvent. Suitable solvents are alcohols such as methanol or ethanol, acetone, acetonitrile, tetrahydrofurane, dioxane, 1,2-dimethoxyethane and 1,2-diethoxyethane.

Suitable electron doners in the present process are in particular sulphinic compounds, phosphine compounds and arsine compounds, for example those described in DT-OS 1,720,906.

As the organic sulphinic compound it is possible to use, in the process according to the invention, any of the organic sulphinic acids in their free form or in the form of a salt or organic ester, as described in V. N. Michailowa et al., Journ. Organ. Chimii, 1, 1621 [1965]; DT-AS 1,145,168; BE-PS 624,071; J. D. Margerum et al., J.Am.Chem. Soc., 93, 3066 [1971]. In addition, esters or adducts of sulphinic acids with carbonyl compounds, especially aldehydes, can be used. Examples of suitable sulphinic acids are p-toluenesulphinic acid, benzenesulphinic acid, p-bromobenzenesulphinic acid, naphthalene-1- or -2-sulphinic acid, 4-acetylaminobenzenesulphinic acid, 2-hydroxybenzene-1-carboxylic acid-5-sulphinic acid, aliphatic sulphinic acids such as ethanesulphinic acid and 1,4-butanedisulphinic acid, and phenylmethanesulphinic acid.

Possible salts of the sulphinic acids are all soluble salts which are compatible with the other components of the light-sensitive solution, for example the sodium salts, potassium salts, lithium salts, magnesium salts, calcium salts, barium salts, silver salts, zinc salts and aluminium salts. Suitable esters of these acids are, in particular, the methyl esters, ethyl esters, propyl esters and butyl esters. Examples of aldehyde adducts of the sulphinic acids are the adducts formed with formaldehyde, acetaldehyde, isobutyraldehyde and heptaldehyde. Further suitable organic sulphinic compounds are the sulphinic acid amides derived from these acids, such as sulphinic acid alkylamides or sulphinic acid arylamides, and the sulphinic acid chlorides.

If phosphines or amines are used as electron donors, then these preferably correspond to the formula

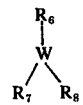 (19)

wherein W denotes a phosphorus or arsenic atom and $R_6$, $R_7$ and $R_8$ independently of one another denote alkyl, aryl, aralkyl or alkylaryl radicals, it being of advantage if at least one of these radicals contains a group which confers solubility in water, for example a hydroxyl, carboxylic acid or sulphonic acid group or a group with a quaternary nitrogen atom.

Suitable phosphines are described in Topics in Phosphorous Chemistry, Vol. 1, ed. by M. Grayson, E. J. Griffith, John Wiley & Sons Inc., page 1 [1964]; ibidem, Vol. 3, page 1; H. J. Bestmann et al:, Angew Chemie 75, 475 [1963]. Suitable arsines are described in W. R. Cullen et al., Chem. Ind. 1963, 983; W. R. Cullen et al., Can. J. Chem. 41, 1625 [1963].

Examples of tertiary organic-substituted phosphines which can be used in the process according to the invention are tributylphosphine, triphenylphosphine, dibutylphenylphosphine, methyldiphenylphosphine and methylbutylphenylphosphine. Examples of suitable tertiary organic-substituted arsine compounds are triphenylarsine, methyldiphenylarsine, trioctylarsine, dibutylphenylarsine and methylbutylphenylarsine.

In general, it is desirable, in the process according to the invention, to use mixtures of preferably water-soluble monomers having a terminal double bond (monofunctional monomers) and those having several terminal double bonds (polyfunctional monomers). It is possible to influence the gel point, that is to say the point at which the polymer becomes insoluble, by using the correct ratio. In particular, the monomer ratio influences the exposure times of the process according to the invention. If the polymerisation does not take place in the liquid phase but in the solid phase, that is to say in a dry layer, the monomer ratio described above influences the adhesion and flexibility of the polymer formed, to its carrier.

Examples of polyfunctional monomers are: N:N''-Alkylenebisacrylamides, secondary acrylamides, tertiary acrylamides, and acrylic acid salts or methacrylic acid salts of divalent or trivalent metals.

Suitable examples of monomers for the process according to the invention are: Alkylenebisacrylamides of the formula

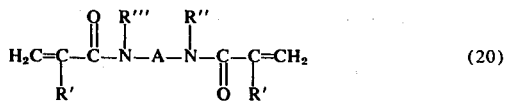

(20)

secondary acrylamides of the formula

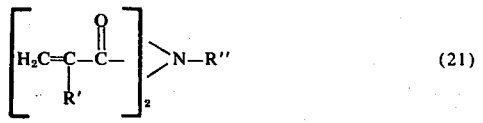

(21)

tertiary acrylamides of the formula

(22)

and salts of monovalent to trivalent metals of the formula

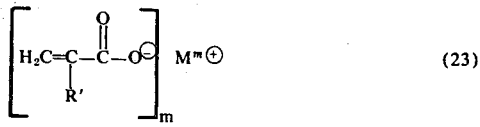

(23)

In the formulae (20) to (23), A denotes an alkylene group with 2 to 6 carbon atoms, R' denotes a hydrogen atom or a methyl group, R'' and R''' each denote a hydrogen atom or an alkyl group with at most 4 carbon atoms, preferably a methyl or ethyl group, M denotes a m-valent metal atom and m is 1, 2 or 3.

Further examples of monomers are: Acrylamide, acrylonitrile, acrylic acid β-hydroxyethylamide, acrylic acid, methacrylic acid, the sodium salts or potassium salts of these acids, calcium diacrylate, barium diacrylate, methacrylamide, methacrylic acid methyl ester, acrylic acid methyl ester, acrylic acid ethyl ester, hydroxymethyldiacetoneacrylamide, diacetoneacrylamide and also vinylpyrrolidone, vinyl methyl ether, vinyl butyl ether, butyric acid vinyl ester, butadiene, isoprene, vinyl chloride and vinylidene chloride.

The radiation to be used in the present process lies in the range of 200 to 450 nm. In other respects, the polymerisation can be carried out in a manner which is in itself known, for example in bulk, in emulsion or in solution. Of course, two or more different monomers can also be copolymerised by this process.

The catalyst system to be used according to the invention is suitable for recording information, especially using the acrylic acids and water-soluble acrylic acid derivatives which have been mentioned, the information, for example in the form of a reproduction of a direct-viewing image or transparent image, first being based on differing degrees of polymerisation and then being easily convertible in a manner which is in itself known into visible images, for example relief images. In one such process for recording information by imagewise exposure of a material in layer form, comprising at least one layer which contains at least one polymerisable ethylenically unsaturated compound, at least one photo-redox pair and optionally a macro-molecular binder, the photo-redox pair used according to the present invention comprises, on the one hand, a diazine compound of the initially indicated composition and, on the other, an organic electron doner, with the radiation serving for the exposure lying in the range of 200 to 450 nm and the polymerisation image being optionally convertible into a relief image or absorption image.

The binder used is preferably a water-soluble colloid. This binder and the remaining constituents of the layer material, in the form of an aqueous solution, are cast on an opaque or transparent carrier to form a layer. The layer thickness is advantageously 1 to 50 μ after drying. In this way, layers of high transparency, which also persists during and after the polymerisation, are produced. Examples of water-soluble colloids which can be used are gelatine, polyvinyl alcohols, poly-N-vinylpyrrolidones and various copolymers of maleic anhydride, inter alia the products commercially available under the descriptions EMA (Monsanto), GANTREZ (GAF), PA resins (Gulf Oil) and SMA (Sinclair Petroleum Inc.).

The exposed image can easily be fixed by washing down or rubbing down with a moist fibrous material, whereby the unexposed and therefore non-polymerised parts are removed.

The colourless relief image can easily be developed to give a coloured image by dipping the material carrying the fixed image into an aqueous or organic dye bath containing a dyestuff which is adsorbed by the image substance or is fixed thereto in some other manner. However, it is simpler if the colouring substance is already incorporated into the casting solution. The colouring substance can be introduced into the casting solution in the monomolecular or colloidal form or as a pigment.

The carrier of the photographically sensitive monomer layer can be modified by suitable processes so as to achieve optimum adhesion of the resulting polymer thereto.

Suitable methods for this purpose are: Surface substration with hardened, originally water-soluble colloids (for example gelatine), addition of wetting agents to the casting solution, surface treatment of the carrier with wetting agents and surface modifications of the carrier by chemical reactions (for example silylation). The sensitivity of the recording material is 1 mJ/cm$^2$ under anaerobic conditions and 0.5 J/cm$^2$ under aerobic conditions.

In addition, this process offers the following advantages:

1. It is found that in comparison to other known processes the system is less sensitive to oxygen. This may be attributable to the production of quinoxaline anion radicals which in turn are strong reducing agents and consume the oxygen present.

2. The redox systems known hitherto have an adverse effect in numerous photographic fields of use because of the visible absorption chromophore of the dyestuff required (US-PS 3,097,096 and DT-OS 1,720,906). These systems are sensitive to daylight and a dark-room is required to handle them. A complicated bleaching process, which reduces the dyestuff employed to its colourless leuco-form, frequently occurs. However, this form is frequently rather unstable and oxidises slowly back to the dyestuff (compare DT-OS 1,720,906).

The quinoxalines have an electromagnetic absorption spectrum in the range from 200 to 400 nm and are therefore mostly colourless compounds; in addition, the $S_o$–$S_1$ band lies in the region of maximum UV emission of numerous mercury high pressure copying lamps. The consequence of this is that after the photopolymerisation a bleaching of the quinoxaline, which acts as one part of the redox pair, is not necessary.

3. The use of this highly active initiator (redox pair) makes it possible to use coloured monomer layers, that is to say it is possible, for example, to produce yellow, magenta and cyan layers without the sensitivity of the material suffering significantly thereby. The cause resides in the position of the quinoxaline absorption band which can cover the minimum of the dyestuff absorption band.

The polymers produced with the initiator system according to the present invention in the presence of the water-soluble colloidal binders are distinguished by outstandingly good physical properties (adhesion to copper, aluminum, triacetate and polyester).

5. The material also works in the absence of organic solvents or of acid or basic aqueous developer systems. It is thus substantially less harmful to the environment than are copying compositions which require organic solvents or acid or basic aqueous developers for their processing (compare DT-OS 2,039,861).

6. The coloured polymers produced on a transparent substrate show excellent properties in respect of point reproduction. Points depicted on the photopolymer can be copied onto suitable substrates without the slightest loss in size or density. This property is of importance in screen reproduction processes.

There now follow manufacturing instructions for diazine compounds.

a. 1,2,3-Trimethyl-6- or -7-methoxyquinoxalinium methosulphate 3.6 g (0.02 mol) of 2,3-dimethyl-6-methoxyquinoxaline are dissolved in 12 ml of freshly distilled dimethyl sulphate and the solution is heated to 60°C for 3 hours in a stream of nitrogen. On slowly cooling, the desired product precipitates from the dark-coloured solution as yellow-brown crystals which are filtered off, washed with dry acetone and subsequently dried. Yield about 2.9 g, corresponding to 47% of theory; melting point: 178°C (decomposition).

The IR (KBr) spectrum and NMR spectrum (D$_2$O) show the bands to be expected from the structure.

b. 1,2,3-Trimethyl-6- or -7-methoxyquinoxalinium perchlorate 1.35 g (0.0043 mol) of 1,2,3-trimethyl-7-methoxyquinoxalinium methosulphate are dissolved in 5 ml of water. 1.7 g (0.0086 mol) of sodium perchlorate in 2 ml of water are added to the solution thus obtain; hereupon, the desired perchlorate separates out immediately. To complete the reaction, the mixture is stirred for a further 15 minutes at room temperature. The precipitate is then filtered off and rinsed with a little cold water. The crystals are purified by taking them up in 20 ml of water and treating the warm solution with active charcoal. After cooling and drying, about 0.6 g (46% of theory) of brown-yellow crystals of melting point 193.1°C are obtained, of which the IR-(KBr) spectrum and NMR (acetoned$_6$) spectrum agree with the structure.

c. 1,2,3-Trimethyl-6,7-dimethoxyquinoxalinium iodide 5.5 g (0.025 mol) of 2,3-dimethyl-6,7-dimethoxyquinoxaline are dissolved in 30 ml of methyl iodide in a 100 ml stirred autoclave. This solution is warmed to 100°C for 24 hours whilst stirring, in the course of which the pressure rises to about 7 atmospheres gauge. After cooling to room temperature, the yellow precipitate is filtered off, rinsed with a little dry acetone and dried. Yield about 6.5 g, corresponding to 72% of theory. Melting point 210° to 212°C (decomposition). The IR (KBr) and NMR (DMSO-d$_6$) spectrum agree with the postulated structure.

The quinoxalinium salts listed in the table can be manufactured analogously. All compounds show, in the IR spectrum and NMR spectrum, the absorption bands to be expected from their structure.

d. 2-Phenylquinoxaline-3'- and -4'-sulphonic acid 72 ml of chlorosulphonic acid are introduced into a reaction vessel equipped with a stirrer, thermometer, condenser and drying tube and are cooled to 0°C. 20 g of 2-phenylquinoxaline are added in portions, whilst keeping the temperature at between 0° and 10°C. The mixture is then allowed to rise to room temperature and is warmed to 90° – 105°C for 8 hours. After cooling, the viscous mass is poured onto 300 g of ice and the mixture is then boiled under reflux until the entire precipitate has dissolved (hydrolysis of the sulphonic acid chloride). After cooling, this solution is extracted by shaking with benzene and is then concentrated continuously. 700 mg of pure 2-phenylquinoxaline-4'-sulphonic acid are first obtained (NMR: All aromatic protons on the benzene ring display ortho- and meta-coupling), whilst finally 1,000 mg of pure 2-phenylquinoxaline-3'-sulphonic acid (NMR: One aromatic proton on the benzene ring shows only metacoupling) are obtained. In total, about 20 g of a mixture of 2-phenylquinoxaline-3'- and -4'-sulphonic acids, which has not melted even at 270°C, are obtained.

The quinoxalines and quinoxalinium salts shown in the table below, which can be used for the process according to the invention, correspond to the formula

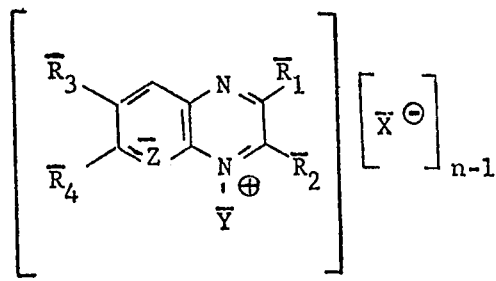

(24)

(No. 1 to 146)

or 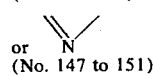

(No. 147 to 151)

*d* denotes decomposition
\* denotes "hydrobromide"
\*\* denotes oil which partially solidifies on standing.

In the case of quinoxalinium salts, only one of the two isomeric forms is indicated in each case. Whether the compound is in the indicated configuration or in its isomeric configuration, was not investigated.

| No. | $\overline{R}_1$ | $\overline{R}_2$ | $\overline{R}_3$ | $\overline{R}_4$ | $\overline{R}_5$ | Y | n | X | Melting point °C | |
|---|---|---|---|---|---|---|---|---|---|---|
| 1 | $C_6H_5$ | $CH_3$ | $CH_3O$ | $CH_3O$ | H | $CH_3$ | 2 | $CH_3SO_4$ | 205–8 | d |
| 2 | $CH_3$ | $C_6H_5$ | H | $CH_3O$ | H | $CH_3$ | 2 | $ClO_4$ | 123–8 | d |
| 3 | $C_6H_5$ | $C_6H_5$ | H | $C_6H_5-CH_2-O$ | H | $CH_3$ | 2 | $ClO_4$ | 120 | d |
| 4 | $CH_3$ | $CH_3$ | $CH_3O$ | $CH_3O$ | $-NO_2$ | $CH_3$ | 2 | $CH_3SO_4$ | 218–22 | d |
| 5 | $C_6H_5$ | $C_6H_5$ | $O-CH_2-CH_2-O$ | | H | $CH_3$ | 2 | $ClO_4$ | 145 | d |
| 6 | $C_6H_5$ | $C_6H_5$ | H | $CH_3O$ | H | $CH_3$ | 2 | $CH_3SO_4$ | 218 | d |
| 7 | $C_6H_5$ | $C_6H_5$ | H | $CH_3O$ | H | $CH_3$ | 2 | $ClO_4$ | 224.8 | |
| 8 | $CH_3$ | $CH_3$ | $CH_3O$ | $CH_3O$ | H | $CH_3$ | 2 | I | 210–2 | d |
| 9 | $4-CH_3O-C_6H_4-$ | $4-CH_3O-C_6H_4$ | H | H | H | $CH_3$ | 2 | $CH_3SO_4$ | 140 | d |
| 10 | $CH_3$ | $CH_3$ | H | $CH_3O$ | H | $CH_3$ | 2 | $CH_3SO_4$ | 178 | d |
| 11 | $CH_3$ | $CH_3$ | H | $CH_3O$ | H | $CH_3$ | 2 | $ClO_4$ | 193.1 | |
| 12 | $C_6H_5$ | $C_6H_5$ | $CH_3O$ | $CH_3O$ | H | $CH_3$ | 2 | $CH_3SO_4$ | 190–4 | d |
| 13 | $C_6H_5$ | $C_6H_5$ | $CH_3O$ | $CH_3O$ | H | $CH_3$ | 2 | $ClO_4$ | 240.9 | |
| 14 | $CH_3$ | $CH_3$ | H | $C_2H_5O$ | H | $CH_3$ | 2 | $CH_3SO_4$ | 149–52 | d |
| 15 | $CH_3$ | $CH_3$ | $CH_3O$ | $CH_3O$ | H | $CH_3$ | 2 | $CH_3SO_4$ | 85–95 | d |
| 16 | $CH_3$ | $CH_3$ | $CH_3O$ | $CH_3O$ | H | $CH_3$ | 2 | $ClO_4$ | 263 | |
| 17 | $C_6H_5$ | $C_6H_5$ | H | $C_2H_5O$ | H | $CH_3$ | 2 | $CH_3SO_4$ | 164–74 | d |
| 18 | $C_6H_5$ | $C_6H_5$ | H | H | $-OCH_3$ | $CH_3$ | 2 | $ClO_4$ | 236–9 | d |
| 19 | $CH_3$ | $CH_3$ | $O-CH_2-O$ | | H | $CH_3$ | 2 | $CH_3SO_4$ | 196 | d |
| 20 | $C_6H_5$ | $CH_3$ | $O-CH_2-O$ | | H | $CH_3$ | 2 | $ClO_4$ | 252 | d |
| 21 | $C_6H_5$ | $C_6H_5$ | $O-CH_2-CH_2-O$ | | H | $CH_3$ | 2 | $CH_3SO_4$ | 212–6 | |
| 22 | $C_6H_5$ | $C_6H_5$ | H | HC=N–CH=CH– (ring) | | $CH_3$ | 2 | $CH_3SO_4$ | 213–7 | d |
| 23 | $CH_3$ | $CH_3$ | H | H | H | — | 1 | — | 106.5 | d |
| 24 | $CH_3$ | $CH_3$ | H | H | H | $CH_3$ | 2 | $ClO_4$ | 199 | |
| 25 | $C_6H_5-CO$ | $C_6H_5-CO$ | H | H | H | — | 1 | — | 171 | d |
| 26 | $C_6H_5-CO$ | H | H | H | H | — | 1 | — | 79.7 | |
| 27 | $C_6H_5$ | $C_6H_5$ | H | H | $OCH_3$ | — | 1 | — | 192.2 | |
| 28 | $CH_3$ | $CH_3$ | H | H | $OCH_3$ | — | 1 | — | 121.6 | |
| 29 | $CH_3$ | $CH_3$ | H | CN | H | — | 1 | — | 205.9 | |
| 30 | $CH_3$ | $CH_3$ | $CH_3O$ | $CH_3-C(=N)-C(H)=C-H$ | | — | 1 | — | 109.4 | |
| 31 | $CH_3$ | $CH_3$ | $O-CH_2-O$ | | H | — | 1 | — | 213.4 | |
| 32 | $C_6H_5$ | $C_6H_5$ | H | $-NO_2$ | H | — | 1 | — | 187.1 | |
| 33 | $CH_3$ | $CH_3$ | H | $-N^+(CH_3)_3$ | H | — | 1 | I | 180–8 | d |

-continued

| No. | $\bar{R}_1$ | $\bar{R}_2$ | $\bar{R}_3$ | $\bar{R}_4$ | $\bar{R}_5$ | $\bar{Y}$ | n | $\bar{X}$ | Melting point °C |
|---|---|---|---|---|---|---|---|---|---|
| 34 | CH₃ | CH₃ | H | HO₃S | H | — | 1 | — | 300 |
| 35 | C₆H₅—CO | C₆H₅—CO | H | H | H | — | 1 | — | 171.3 |
| 36 | CH₃ | CH₃ | CH₃O | CH₃O | NO₂ | — | 1 | — | 177.2 |
| 37 | CH₃ | CH₃ | H | C₂H₅—O | H | — | 1 | — | 108.9 |
| 38 | C₆H₅ | C₆H₅ | H | CH₃ | H | CH₃ | 2 | ClO₄ | 250.8 |
| 39 | CH₃ | CH₃ | H | NH₂ | H | — | 1 | — | 191.9 |
| 40 | C₆H₅ | CH₃ | CH₃O | CH₃O | H | — | 1 | — | 150.5 |
| 41 | —CH₂OH | —CH₂OH | | O—CH₂—CH₂O | H | — | 1 | — | 180.8 |
| 42 | —CH₂OH | —CH₂OH | CH₃O | CH₃O | H | — | 1 | — | 183.7 |
| 43 | CH₂OH | CH₂OH | | O—CH₂—O | H | — | 1 | — | 198.5 |
| 44 | C₆H₅ | C₆H₅ | H | H | H | CH₃ | 2 | ClO₄ | 145.7 |
| 45 | CH₃ | CH₃ | H | CH₃ | H | CH₃ | 2 | ClO₄ | 194 |
| 46 | C₆H₅ | C₆H₅ | H | Cl | H | CH₃ | 2 | ClO₄ | 209.3 |
| 47 | C₆H₅ | C₆H₅ | H | CN | H | — | 1 | — | 181.4 |
| 48 | CH₃ | CH₃ | H | CON(C₂H₅) | H | — | 1 | — | 73.3 |
| 49 | C₆H₅ | C₆H₅ | H | CON(C₂H₅) | H | — | 1 | — | 137.0 |
| 50 | CH₃ | CH₃ | NH₂ | CH₃O | H | — | 1 | — | 252 |
| 51 | CH₃ | CH₃ | H | CO—OC₂H₅ | H | — | 1 | — | 100.6 |
| 52 | C₆H₅ | C₆H₅ | H | CO—OC₂H₅ | H | — | 1 | — | 151.9 |
| 53 | CH₃ | CH₃ | H | CH₃O | NHCO CH₃ | — | 1 | — | 183.9 |
| 54 | C₆H₅ | C₆H₅ | CH₃O | CH₃O | H | — | 1 | — | 252.4 |
| 55 | CH₃ | CH₃ | CH₃O | CH₃O | H | — | 1 | — | 178.1 |
| 56 | C₆H₅ | C₆H₅ | H | CH₃O | Cl | — | 1 | — | 186.4 |
| 57 | CH₃ | CH₃ | H | CH₃O | Cl | — | 1 | — | 147.3 |
| 58 | C₆H₅ | C₆H₅ | H | Cl | OCH₃ | — | 1 | — | 140.0 |
| 59 | C₆H₅ | C₆H₅ | H | CO—OCH₃ | H | — | 1 | — | 290.3 |
| 60 | C₆H₅ | C₆H₅ | H | CO—OCH₃ | H | — | 1 | — | 290.3 |
| 61 | CH₃ | CH₃ | H | CO—OCH₃ | H | — | 1 | — | 262.6 |
| 62 | C₆H₅ | C₆H₅ | H | C₂H₅O | H | — | 1 | — | 154.3 |
| 63 | CH₃ | CH₃ | H | CH₃O | H | — | 1 | — | 88.6 |
| 64 | CH₃ | C₆H₅ | H | CH₃O | H | — | 1 | — | 122.0 |
| 65 | C₆H₅ | C₆H₅ | H | CH₃O | H | — | 1 | — | 160.8 |
| 66 | CH₃ | CH₃ | H | CH₃O | H | — | 1 | — | 100.3 |
| 67 | C₆H₅ | C₆H₅ | H | C₄H₉O | H | — | 1 | — | 144.0 |
| 68 | CH₃ | CH₃ | H | CH₃O | NHC=O C₆H₅ | — | 1 | — | 196.3 |
| 69 | CH₃ | CH₃ | H | CONH₂ | H | — | 1 | — | 250 |
| 70 | C₆H₅ | C₆H₅ | H | COOCH₃ | H | — | 1 | — | 145.2 |
| 71 | C₆H₅ | C₆H₅ | H | CONH₂ | H | — | 1 | — | 254.2 |
| 72 | CH₃ | CH₃ | H | Cl | OCH₃ | — | 1 | — | 50.4 |
| 73 | CH₃ | CH₃ | H | C₄H₉O | H | — | 1 | — | 50.4 |
| 74 | CH₃ | CH₃ | H | CH₃O | NO₂ | — | 1 | — | 150.1 |
| 75 | CH₃ | CH₃ | H | C₂H₅O | NO₂ | — | 1 | — | 144.2 |
| 76 | CH₃ | CH₃ | H | CH₃O | NH₂ | — | 1 | — | 135.7 |
| 77 | CH₃ | CH₃ | | O—CH₂—O | H | — | 1 | — | 213.3 |
| 78 | CH₃ | C₆H₅ | | O—CH₂—O | H | — | 1 | — | 125.2 |
| 79 | CH₃ | CH₃ | H | O—CH₂—O | | — | 1 | — | 154.5 |
| 80 | CH₃ | CH₃ | H | O—CH₂—CH₂—O | | — | 1 | — | 141.3 |
| 81 | C₆H₅ | C₆H₅ | | O—CH₂—CH₂—O | H | — | 1 | — | 225.0 |
| 82 | C₆H₅ | C₆H₅ | | O—CH₂—O | H | — | 1 | — | 152.7 |
| 83 | C₆H₅ | C₆H₅ | H | O—CH₂—O | | — | 1 | — | 136.9 |
| 84 | CH₃ | CH₃ | | O—CH₂—CH₂—O | H | — | 1 | — | 189.9 |
| 85 | CH₃ | C₆H₅ | | O—CH₂—CH₂—O | H | — | 1 | — | 105.6 |
| 86 | C₆H₅ | C₆H₅ | H | O—CH₂—CH₂—O | | — | 1 | — | 192.2 |
| 87 | CH₂Br | CH₂Br | CH₃O | C H₃O | H | — | 1 | — | 185.6 |
| 88 | CH₂—OH | CH₂—OH | CH₃O | CH₃O | H | — | 1 | — | 121.5 |
| 89 | CH₂OH | CH₂OH | CH₃O | CH₃O | H | — | 1 | — | 183.7 |
| 90 | CH₂OCH₃ | CH₂OCH₃ | H | H | H | — | 1 | — | Boiling point at 0.08 mm Hg 103-5 |
| 91 | CH₂—N(CH₃)₂ | CH₂N(CH₃)₂ | CH₃CONH | CH₃O— | H | — | 1 | — | 198-9 d |
| 92 | CH₂—SCH₃ | CH₂SCH₃ | H | Cl | H | — | 1 | — | 122.8 |
| 93 | CH₂Br | CH₂Br | CH₃CONH | CH₃O | H | — | 1 | — | 214-5 |
| 94 | CH₂—O—CO—CH₃ | CH₂—O—CO—CH₃ | | O—CH₂—O | H | — | 1 | — | 138.7 |
| 95 | CH₂Br | CH₂Br | | O—CH₂—CH₂— | H | — | 1 | — | 180-90 d |
| 96 | CH₂—OCOCH₃ | CH₂—OCOCH₃ | | O—CH₂—CH₂—O | H | — | 1 | — | 187 d |
| 97 | CH₂Br | CH₂Br | | O—CH₂—OH | H | — | 1 | — | 187.5 |
| 98 | CH₂—OCOCH₃ | CH₂—OCOCH₃ | H | H | H | — | 1 | — | 85.1 |
| 99 | CH₂Br | CH₂Br | H | Cl | H | — | 1 | — | 143.3 |
| 100 | CH₂Br | CH₂Br | H | CH₃O | Cl | — | 1 | — | 165.7 |
| 101 | CH₂Br | CH₂Br | H | Cl | CH₃O | — | 1 | — | 93.6 |
| 102 | CH₂Br | CH₂Br | H | H | CH₃O | — | 1 | — | 155.6 |
| 103 | CH₂Br | CH₂Br | H | H | H | — | 1 | — | 155.0 |
| 104 | CH₂Br | CH₂Br | H | COOC₂H₅ | H | — | 1 | — | 85.0 |
| 106 | CH₂—OCOCH₃ | CH₂—OCOCH₃ | H | COOC₂H₅ | H | — | 1 | — | 94.3 |
| 107 | CH₂—OCOCH₃ | CH₂—OCOCH₃ | H | CH₃O | H | — | 1 | — | 71.8 |
| 108 | CH₂—OCOCH₃ | CH₂—OCOCH₃ | H | H | CH₃O | — | 1 | — | 80.3 |
| 109 | CH₂OH | CH₂OH | H | H | H | — | 1 | — | 162.6 |
| 110 | CH₂OH | CH₂OH | H | COOK | H | — | 1 | — | >300 |
| 111 | CH₂OH | CH₂OH | H | CH₃O | H | — | 1 | — | **) |
| 112 | CH₂Br | CH₂Br | H | NO₂ | H | — | 1 | — | 114.5 |
| 113 | CH₂OH | CH₂OH | | O—CH₂—CH₂—O | H | — | 1 | — | 180.8 |

-continued

| No. | $\bar{R}_1$ | $\bar{R}_2$ | $\bar{R}_3$ | $\bar{R}_4$ | $\bar{R}_5$ | $\bar{Y}$ | n | $\bar{X}$ | Melting point °C | |
|---|---|---|---|---|---|---|---|---|---|---|
| 114 | $CH_2-OCOCH_3$ | $CH_2-OCOCH_3$ | H | $NO_2$ | H | — | 1 | — | 122.8 | |
| 115 | $CH_2-OCOCH_3$ | $CH_2-OCOCH_3$ | H | $CH_3O$ | Cl | — | 1 | — | 107.3 | |
| 116 | $CH_2-OCOCH_3$ | $CH_2-OCOCH_3$ | H | Cl | $CH_3O$ | — | 1 | — | 99.6 | |
| 117 | $CH_2OH$ | $CH_2OH$ | H | $CH_3O$ | Cl | — | 1 | — | 179.3 | |
| 118 | $CH_2OH$ | $CH_2OH$ | H | Cl | $CH_3O$ | — | 1 | — | 112.6 | |
| 119 | $CH_2-S-C(NH)(NH_2)$ | $CH_2-S-C(NH)(NH_2)$ | | $O-CH_2-CH_2-O$ | H | — | 1 | — | *) | |
| 120 | $CH_2-S-C(NH)(NH_2)$ | $CH_2-S-C(NH)(NH_2)$ | H | H | H | — | 1 | 13 | *) | |
| 121 | $CH_2-SC_4H_9$ | $CH_2-SC_4H_9$ | H | H | H | — | 1 | — | 55.8 | |
| 122 | $CH_2-S-C(H_3C)(CH_3)-S-CH_2$ | | H | H | H | — | 1 | — | 195.5 | |
| 123 | $CH_2-SCOCH_3$ | $CH_2-SCOCH_3$ | H | H | H | — | 1 | — | 105.9 | |
| 124 | $CH_2Cl$ | $CH_2Cl$ | H | H | H | — | 1 | — | 148.8 | |
| 125 | $CH_2Cl$ | $CH_2Cl$ | H | H | $CH_3$ | — | 1 | — | 110.3 | |
| 126 | $CH_2Br$ | $CH_2Br$ | H | $C_4H_9$ | H | — | 1 | — | **) | |
| 127 | $CH_2-OCOCH_3$ | $CH_2-OCOCH_3$ | H | $C_4H_9$ | H | — | 1 | — | **) | |
| 128 | $CH_2OH$ | $CH_2OH$ | H | $C_4H_9$ | H | — | 1 | — | **) | |
| 129 | $CH_2OH$ | $CH_2OH$ | $NH_2$ | $CH_3O$ | H | — | 1 | — | 158 | |
| 130 | $CH_2Cl$ | $CH_2Cl$ | H | HO | H | — | 1 | — | 172–174 | d |
| 131 | $CH_2OH$ | $CH_2OH$ | NH(COCH_3) | $CH_3O$ | H | — | 1 | — | 236.3 | |
| 132 | $CH_2-OCOCH_3$ | $CH_2-OCOCH_3$ | NH(COCH_3) | $CH_3O$ | H | — | 1 | — | 158.0 | |
| 133 | $-CH_2-C(NC)(COOC_2H_5)-CH-$ | | H | H | H | — | 1 | — | 146.3 | |
| 134 | $CH_3$ | $CH_3$ | H | $CH_3-O$ | H | $CH_3$ | 2 | $PF_6$ | 149–152 | d |
| 135 | $C_6H_5$ | $C_6H_5$ | H | $CH_3$ | H | $CH_3$ | 2 | $PF_6$ | 124–129 | d |
| 136 | $C_6H_5$ | $C_6H_5$ | H | $CH_3$ | H | $CH_3$ | 2 | $PF_6$ | 214–218 | d |
| 137 | $C_6H_5$ | $C_6H_5$ | H | $CH_3$ | H | $CH_3$ | 2 | $BF_4$ | 238–239 | d |
| 138 | $C_6H_5$ | $C_6H_5$ | H | $CH_3$ | H | $CH_3$ | 2 | $AsF_6$ | 223–229 | d |
| 139 | $C_6H_5$ | $C_6H_5$ | H | $CH_3-O$ | H | $CH_3$ | 2 | $PF_6$ | 213–216 | |
| 140 | $C_6H_5$ | $C_6H_5$ | H | $CH_3-O$ | H | $CH_3$ | 2 | $BF_4$ | 208–209 | |
| 141 | $C_6H_5$ | $C_6H_5$ | H | $CH_3-O$ | H | $CH_3$ | 2 | $AsF_6$ | 215–217 | |
| 142 | $C_6H_5$ | $C_6H_5$ | H | $CH_3-O$ | H | $CH_3$ | 2 | Cl | 174 | d |
| 143 | $C_6H_5$ | $C_6H_5$ | H | Cl | H | $CH_3$ | 2 | $PF_6$ | 209–212 | d |
| 144 | $C_6H_5$ | $C_6H_5$ | $CH_3O$ | $CH_3-O$ | H | $CH_3$ | 2 | Cl | 205–209 | d |
| 145 | $C_6H_5$ | $C_6H_5$ | H | $CH_3$ | H | $CH_3$ | 2 | Cl | 224 | d |
| 146 | $CH_2-O-COCH_3$ | $CH_2-O-COCH_3$ | | $O-CH_2-O$ | | $=C(H)(-)$ | 2 | $FSO_3$ | 135–145 | d |
| 147 | $CH_3$ | $CH_3$ | Br | H | | N | 1 | — | 141.7 | |
| 148 | $C_6H_5$ | $C_6H_5$ | Br | H | | N | 1 | — | 126–129 | |
| 149 | $C_6H_5$ | $C_6H_5$ | H | H | | N | 1 | — | 143.4 | |
| 150 | $CH_3$ | $CH_3$ | H | H | | N | 1 | — | 144.4 | |
| 151 | $CH_3$ | $CH_3$ | H | OH | | N | 1 | — | 203.6 | |

EXAMPLE 1

A cellulose triacetate film of size 234 cm², coated with hardened gelatine, is covered with 4 ml of the solution shown below (casting solution 1), to which, before casting, 10 mg of the quinoxaline compound of the formula

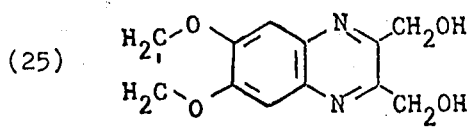

(25)

in 2 ml of ethanol and 2 ml of an 0.016 molar aqueous sodium p-toluenesulphinate solution have also been added, and is dried.

Casting solution 1

180 ml of 1.4 molar aqueous barium diacrylate solution
60 ml of 1.6 molar aqueous acrylamide solution
30 ml of 6% strength aqueous gelatine
30 ml of 0.25% strength aqueous solution of a nonionic polyfluorinated wetting agent (FC 170 from 3 M).

The film treated in this way is exposed under a photographic step wedge (12 steps) for 30 seconds by the contact process to a 400 watt mercury high pressure lamp at a distance of 40 cm. Thereafter the film is washed with water or rubbed down with moist cotton-wool and subsequently immersed for 10 seconds in a 2% strength aqueous solution of the dyestuff of the formula

(26) 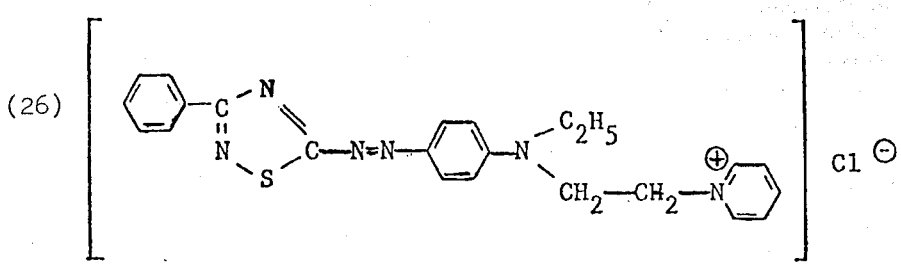 Cl⊖

The film strip is then briefly washed with water and dried. All 12 wedge steps are clearly recognisable. The maximum colour density is about 3.2.

EXAMPLE 2

The procedure indicated in Example 1 is followed, but using the quinoxaline compound of the formula

(27) 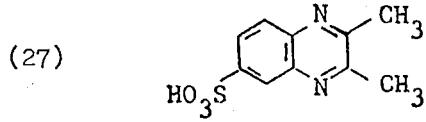

and a similar result is obtained. This is also true of the quinoxaline compound of the formula

(28) 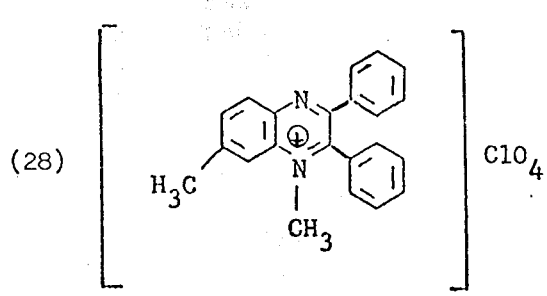 ClO₄⊖

Analogous results are obtained if a different quinoxaline derivative, listed in the table, is employed in suitable amounts.

EXAMPLE 3

The procedure indicated in Example 1 is followed, using one of the quinoxaline compounds listed in Example 1 or 2, but employing the following casting solution:

Casting solution 2

90 ml of an 0.6% strength aqueous methylene-bisacrylamide solution ($H_2C=HC-OC-HN-CH_2-NH-CO-CH=CH_2$)
90 ml of a 20% strength aqueous acrylamide solution
45 ml of a 6% strength aqueous gelatine
30 ml of an 0.25% strength aqueous solution of a non-ionic polyfluorinated wetting agent (FC 170 from 3M).

After exposure and rubbing down with moist cotton-wool, a polymer core corresponding to the original results.

EXAMPLE 4

The procedure indicated in Example 1 is followed, with the sole difference that instead of p-toluenesulphinate 2 ml of an 0.02 molar aqueous solution of sodium diphenylphosphinobenzene-m-sulphonate (see Ahrland et al. J. Chem. Soc., 1958, 281), is used and in this way an image with 12 step wedges which can be differentiated is again obtained.

Instead of the sulphinate or of the phosphine compound, triphenylarsine can also be employed.

EXAMPLE 5

If, in producing the image according to Example 1, instead of subsequently treating the film with the dyestuff solution, 1 ml of a 2% strength aqueous solution of the dyestuff of the indicated formula is added to the casting solution 1, the excess dyestuff can easily be removed, after exposure, by washing off or wiping off. With this procedure, all 12 wedge steps again show different colour intensities. The maximum colour density is 1.5 to to 2.

EXAMPLE 6

One of the casting solutions 3 to 9 described below is employed in each case.

Casting solution 3

180 ml of a 1.4 molar aqueous barium diacrylate solution
60 ml of a 1.6 molar acrylamide solution in ethanol
30 ml of a 6% strength aqueous gelatine 30 ml of an 0.25% strength aqueous solution of a non-ionic wetting agent, for example an addition product of ethylene oxide to nonylphenol, a lauric acid ethanolamide, a stearic acid alkanolamide or diglycol stearate.

Casting solution 4

100 ml of a 1.4 molar aqueous barium diacrylate solution
38 g of acrylamide dissolved therein
6 g of gelatine
2 ml of a 8% strength aqueous wetting agent solution (non-ionic)

Casting solution 5

4 g of ethylene-maleic anhydride resin
3 g of acrylamide
0.6 g of methylene-bis-acrylamide [$H_2C$—(H-N—OC—CH=$CH_2$)$_2$]
45 ml of water
5 ml of an 0.25% strength aqueous wetting agent solution (non-ionic)

Casting solution 6

4 g of ethylene-maleic anhydride resin
3 g of acrylamide
1 g of acrylic acid 1,1-dimethyl-3-oxobutylamide
0.6 g of methylenebisacrylamide
5 ml of an 0.25% strength aqueous wetting agent solution

Casting solution 7

165 ml of a 1.4 molar aqueous barium diacrylate solution
6.23 g of acrylamide
350 ml of a 40% strength aqueous solution of a high molecular polyvinyl alcohol (degree of saponification 98%)
10 ml of an 8% strength wetting agent solution

Casting solution 8

3.53 g of polyacrylamide (molecular weight $1 \times 10^6$ to $3 \times 10^6$)
80 ml of a 1.4 molar aqueous barium diacrylate solution
3.03 g of acrylamide
5 ml of an 8% strength aqueous wetting agent solution
160 ml of water

Casting solution 9

3.53 g of polyacrylamide (molecular weight $1 \times 10^6$ to $3 \times 10^6$)
0.3 g of methylenebisacrylamide
6 g of acrylamide
1 g of α-hydroxymethylated acrylic acid 1,1-dimethyl-3-oxobutylamide A solution of 70 mg of quinoxaline No. 113 from the table, in 14 ml of ethanol, is combined with 14 ml of an 0.02 molar aqueous solution of sodium p-toluenesulphinate. 5 ml of one of the casting solutions 3 to 9 are added to 4 ml of this solution. The mixture is cast on a triacetate or polyester carrier provided with a hardened gelatine layer so that after drying a layer thickness of 1 to 10 μm results. The dried, transparent layer is exposed for 30 seconds by the contact process under a half tone 12-step wedge, using a 400 watt mercury high pressure lamp. The exposed material is then washed with water or rubbed down with moist cottonwool. The original, with 12 distinguishable steps, can be detected as a half-tone surface on the film. The height of the surface half-tone pattern can be controlled by the exposure time.

The half-tone images produced in this way with the aid of the casting solutions 3, 4, 7 or 8 can be converted by substantive dyeing into coloured images which correspond to a negative of the original. For this purpose, the film carrying the half-tone image is dipped for 5 to 30 seconds into a 2 to 5% strength aqueous solution of the dyestuff of the formula (26). The film is then washed briefly. All half-tone dots consisting of a charged polymer are dyed.

In all cases, it is possible to obtain similar results by using, instead of the diazine compound No. 113, one of the following diazine compounds: No. 8, 10, 11, 23, 26, 27, 28, 30, 31, 32, 33, 34, 36, 37, 38, 39, 40, 43 and 88, a 2-phenylquinoxaline-3'- and -4'-sulphonic acid mixture (see manufacturing instruction (d)), 2-phenylquinoxaline-6- or -7-sulphonic acid, 2,3-dimethyl-5,8-dimethoxyquinoxaline or 2,3-dimethyl-5,8-dihydroxyquinoxaline.

Similar results are also obtained if, in casting solutions 3, 4,, 7 or 8, the barium diacrylate is replaced by calcium diacrylate or strontium diacrylate.

Equally it is possible, using one of the casting solutions 3 to 9 and one of the abovementioned diazine compounds, to utilise the following as electron donors instead of p-toluenesulphinate for producing an image in the indicated manner: Sodium diphenyl-phosphino-benzene-m-sulphonate, triphenylarsine and sodium diphenylphosphinopropanesulphonate.

EXAMPLE 7

1 ml of a 3% strength solution of the dyestuff of the formula (26) is added to the casting solution of Example 6 (casting solution 3, diazine No. 113). The solution cast in this way gives a transparent red layer of colour density 4. After 2 minutes' exposure through a half-tone step wedge, the material is washed briefly. All half-tone dots of the original are depicted directly. The image displays a maximum colour density of 2.

EXAMPLE 8

1 ml of a 2% strength solution of the dyestuff of the formula

(27) 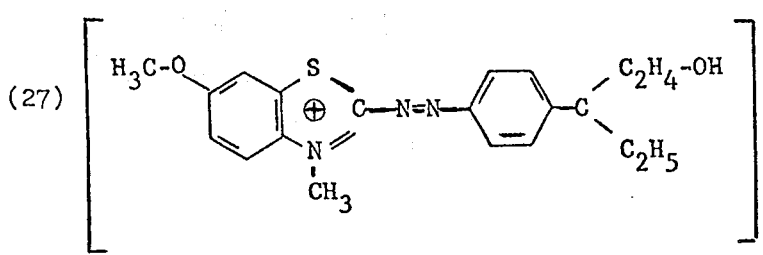 

is added to the casting solution of Example 6. After exposure for 4 minutes through a screen, the blue layer thereby obtained is washed briefly or rubbed down moist, the original being depicted on the substrate as a negative in a blue colour.

EXAMPLE 9

100 mg of a red pigment dyestuff are distributed ultrasonically in the casting solution of Example 1, using an ultrasonic disperser. The completely transparent cast solution gives a clear layer. After 4 minutes' exposure through a 12-step half-tone wedge, the film is rubbed down with a moist cottonwool pad. All 12 half-tone steps are distinguishable.

In distinction to the preceding examples, the polymerisation can also be carried out in the absence of a macromolecule such as polyacrylamide, gelatine and polyvinyl alcohol. In this case, the casting solutions 3 to 9 can be polymerised under the action of light without the macromolecular substance in solutions containing water and/or ethanol. Using this method or that described in the examples which follow, it is possible to produce transparent polymers which can be swollen with water and can be used, for example, for medicinal purposes or be converted into other products, such as inks, lacquers, paints, coatings or mouldings.

Example 10

30 g of acrylamide and 1 g of methylenebisacrylamide are dissolved in 50 ml of ethanol-water (1:1). 100 g of 2-phenylquinoxaline and 100 mg of triphenylphosphine, dissolved in 10 ml of ethanol, are added. After a short period of exposure to a 200 watt mercury high pressure lamp, the polymer which forms, and which is insoluble in ethanol, begins to flocculate. Instead of triphenylphosphine, equal amounts of triphenylarsine or p-toluenesulphinic acid can be employed as electron donors.

The following quinoxalines can also be used instead of 2-phenylquinoxaline: Quinoxaline, 2-benzoyl-3-methylquinoxaline, 2-benzoyl-3-phenylquinoxaline, 2-acetyl-3-methyl-quinoxaline, 2,3-dimethyl-5,8-dimethoxyquinoxaline or one of the compounds No. 23, 27, 37 and 113. Similar results are obtained.

Example 11

30 g of acrylamide, 1 g of methylene-bisacrylamide and 1 g of diacetone-acrylamide are dissolved in 50 ml of water. 200 g of 2-phenylquinoxaline-3'- and -4'-sulphonic acid and 200 mg of sodium p-toluenesulphinate are added. After a short exposure time at room temperature, using a 200 W mercury high pressure lamp. the viscosity of the solution begins to rise markedly. If the process is carried out under a nitrogen atmosphere or argon atmosphere at 5°C, the rise in viscosity is considerably more rapid still.

Instead of the indicated phenylquinoxalinesulphonic acid, 2-phenylquinoxaline-3'-sulphonic acid, 2-phenylquinoxaline-4'-sulphonic acid, 2,3-dimethylquinoxaline-6-sulphonic acid or 2-phenylquinoxaline-6,7-sulphonic acid mixture can also be used, with similar results.

What we claim is:

1. Process for the photopolymerisation of ethylenically unsaturated monomers which contain terminal $H_2C=$ groups and are water-soluble with the aid of at least one photoredox pair, which comprises employing as redox pair, on the one hand, a diazine compound of the formula

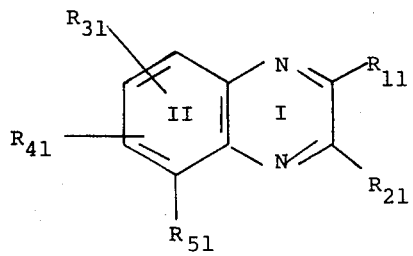

wherein $R_{11}$ and $R_{21}$ denote a phenyl radical, a benzoyl radical, a phenylsulphonic acid group a methyl group or a hydrogen atom, or $R_{11}$ and $R_{21}$ together with two carbon atoms of the ring I denote a five-membered or six-membered heterocyclic and $R_{31}$, $R_{41}$ and $R_{51}$ denote a hydrogen atom, or lower alkyl group, a chlorine atom, a nitro group, a primary amino group, an acylamino group, a trimethylammonium group, a carboxylic acid amide group which is not substituted further or is substituted further by one to two lower alkyl groups, a carboxylic acid group, carboxylic acid methyl ester group or carboxylic acid ethyl ester group or sulphonic acid group, or two of $R_{31}$, $R_{41}$ and $R_{51}$ together with two adjoining carbon atoms of the ring II denote an heterocyclic ring, and on the other hand, an electron donor, and using for the photopolymerisation a radiation which lies in the range of 200 to 450 nm.

2. Process according to claim 1 which comprises employing a diazine compound of the formula

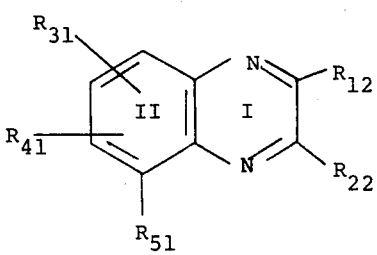

wherein
$R_{31}$, $R_{41}$ and $R_{51}$ have the meaning given in claim 1 and $R_{12}$ and $R_{22}$ denote a phenyl group, a benzoyl radical, a phenylsulphonic acid group, a hydroxymethyl group or a hydrogen atom.

3. Process according to claim 1 which comprises employing a diazine compound of the formula

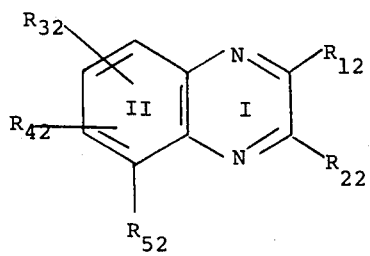

wherein
$R_{12}$ and $R_{22}$ denote a phenyl radial, a benzoyl radical, a phenylsulphonic acid group, a hydroxymethyl group or a hydrogen atom and
$R_{32}$, $R_{42}$ and $R_{52}$ denote a hydrogen atom or a methyl, methoxy, ethoxy, nitro, amino, acetylamino, trimethylammonium or sulphonic acid group, or two of $R_{32}$, $R_{42}$ and $R_{52}$ together with two adjoining carbon atoms of the ring II denote an heterocyclic ring.

4. Process according to claim 3 which comprises employing a diazine compound of the formula

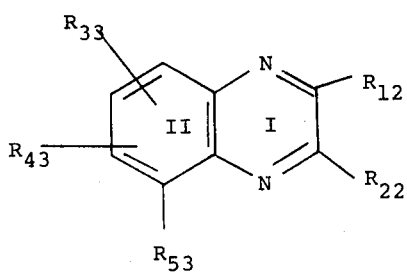

wherein
$R_{12}$ and $R_{22}$ denote a phenyl radical, a benzoyl radical, a phenysulphonic acid group, a hydroxymethyl group or a hydrogen atom and
$R_{33}$, $R_{43}$ and $R_{53}$ denote a hydrogen atom or a methyl, methoxy, ethoxy, nitro, amino, trimethylammonium or sulphonic acid group, or two of $R_{33}$, $R_{43}$ and $R_{53}$ together with two adjoining carbon atoms of the ring II denote a dioxole, dioxane or pyridine ring.

5. Process according to claim 3 which comprises employing the diazine compound of the formula

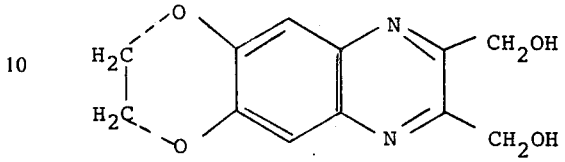

6. Process for recording information by image-wise exposure of a material in layer form possessing at least one layer which contains at least one polymerisable ethylenically unsaturated compound, at least one photoredox pair and optionally a macromolecular binder, which process comprises using a photoredox pair which consists, on the one hand, of a diazine compound of the composition indicated in claim 3 and, on the other, of an organic electron donor and the radiation used for exposure lies in the range from 200 to 450 nm.

7. Process according to claim 6, which comprises using as a binder gelatine, chemically modified gelatine, a polyvinyl alcohol, copolymers of maleic anhydride, methylcellulose, polyacrylamide or polyvinyl-N-pyrrolidone.

8. Process according to claim 1, which comprises employing a sulphinic compound as the electron donor.

9. Process according to claim 8, which comprises employing a free sulphinic acid as the electron donor.

10. Process according to claim 8, which comprises employing as the electron donor a salt of a sulphinic acid or an ester of a sulphinic acid which is derived from an aliphatic alcohol.

11. Process according to claim 1, which comprises employing as the electron donor a phosphine or arsine of the formula

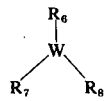

wherein W denotes a phosphorus or arsenic atom and $R_6$, $R_7$ and $R_8$ independently of one another denote alkyl, aryl, aralkyl or alkylaryl groups.

12. Process according to claim 11, wherein at least one of the radicals $R_6$, $R_7$ and $R_8$ possesses a group which confers solubility in water.

13. Photopolymerisable composition, which contains at least one polymerisable ethylenically unsaturated compound, at least one photo redox pair and a macromolecular binder, wherein the photoredox pair consists of a diazine compound of the composition indicated in claim 1 and an electron donor.

14. Photopolymerisable composition according to claim 13, which contains a dyestuff in a finely dispersed or colloidal form.

* * * * *